United States Patent
Osborn, III et al.

[11] Patent Number: 6,152,905
[45] Date of Patent: Nov. 28, 2000

[54] ABSORBENT INTERLABIAL DEVICE COMPRISING A FLUID ACQUISITION/TRANSFER COMPLEX

[75] Inventors: Thomas W. Osborn, III, Cincinnati; Ronald B. Visscher, Glendale, both of Ohio

[73] Assignee: The Procter & Gamble Company, Cincinnati, Ohio

[21] Appl. No.: 08/949,109

[22] Filed: Oct. 10, 1997

[51] Int. Cl.[7] ........................................ A61F 13/15
[52] U.S. Cl. ...................... 604/378; 604/385.1; 604/904; 604/370
[58] Field of Search .................... 604/363, 378, 604/385.1, 904

[56] References Cited

U.S. PATENT DOCUMENTS

| | | |
|---|---|---|
| 2,917,049 | 12/1959 | Delaney . |
| 3,695,270 | 10/1972 | Dostal . |
| 3,726,277 | 4/1973 | Hirschman . |
| 5,762,644 | 6/1998 | Osborn, III et al. . |

FOREIGN PATENT DOCUMENTS

| | | |
|---|---|---|
| 0 597 498A1 | 5/1994 | European Pat. Off. . |
| WO 95/15138 | 6/1995 | WIPO . |
| WO 96/07379 | 3/1996 | WIPO . |
| WO 96/16626 | 6/1996 | WIPO . |
| WO 97/23183 | 7/1997 | WIPO . |
| WO 98/08475 | 3/1998 | WIPO . |

*Primary Examiner*—John G. Weiss
*Assistant Examiner*—Dennis Ruhl
*Attorney, Agent, or Firm*—Theodore P. Cummings; Jeffrey V. Bamber; Jacobus C. Rasser

[57] ABSTRACT

The present invention provides an absorbent device insertable into the interlabial space of a female wearer. The absorbent device comprises a main absorbent portion comprising an upper portion and a lower portion. The upper portion has a top surface facing toward the vestibule floor of the wearer during insertion into the interlabial space. The upper portion leads the lower portion during insertion of the absorbent device; i.e., the lower portion is spatially opposed to the upper portion, and upon insertion of the absorbent device into a wearer's interlabial space, the lower portion faces away from the vestibule floor of the wearer. Additionally, a fluid acquisition/transfer complex is positioned about and extends at least from the upper portion of the main absorbent portion. The fluid acquisition/transfer complex is configured to be in intimate contact with the folds and creases of the interlabial space of the female wearer. Furthermore, the fluid acquisition/transfer complex receives fluid from the folds and creases of a wearer's interlabial space and transfers fluid to the main absorbent portion.

29 Claims, 2 Drawing Sheets

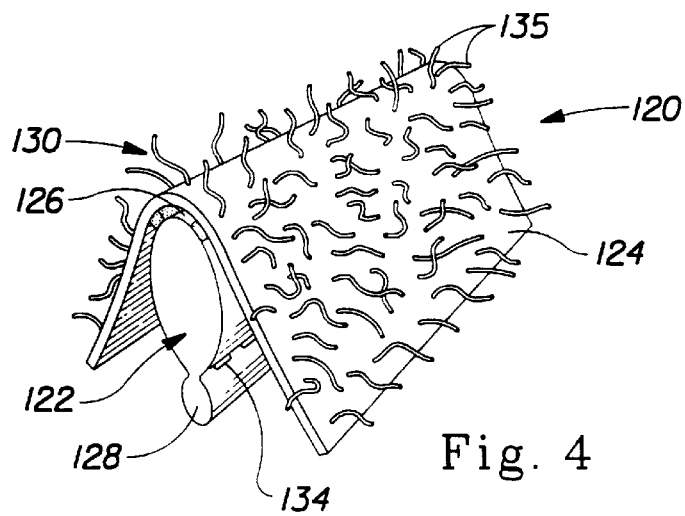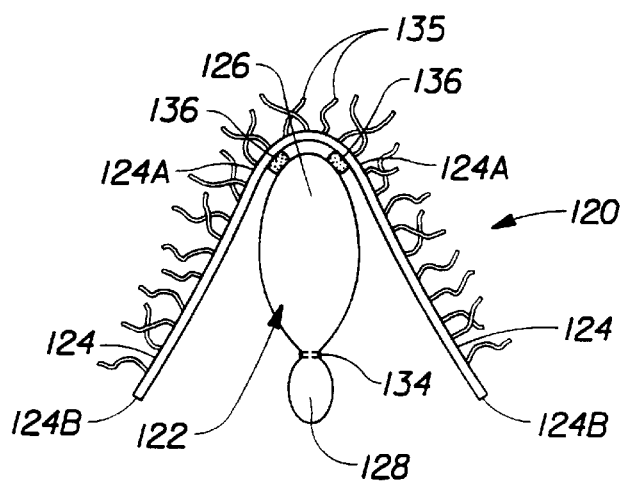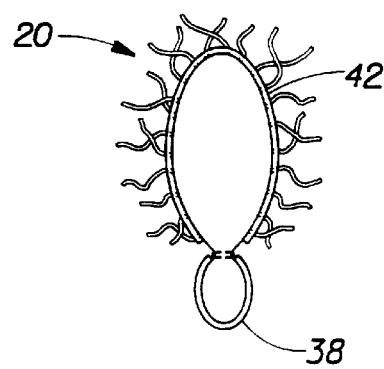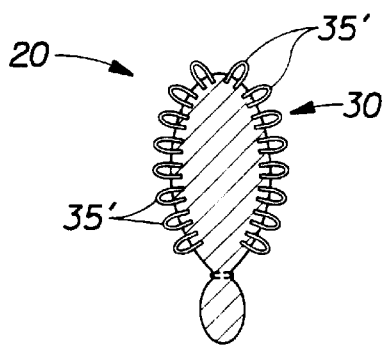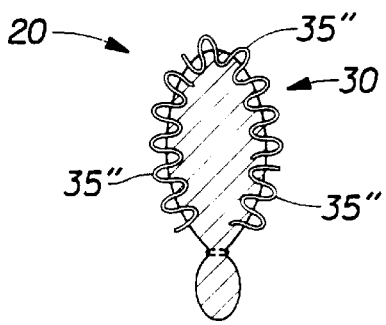

ABSORBENT INTERLABIAL DEVICE COMPRISING A FLUID ACQUISITION/TRANSFER COMPLEX

FIELD OF THE INVENTION

This invention relates to absorbent devices that are worn interlabially by female wearers for catamenial purposes, incontinence protection, or both.

BACKGROUND OF THE INVENTION

All manner and variety of absorbent articles configured for the absorption of body fluids such as menses, urine and feces are, of course, well known. With respect to feminine protection devices, the art has offered two basic types; sanitary napkins have been developed for external wear about the pudendal region while tampons have been developed for internal wear within the vaginal cavity for interruption of menstrual flow therefrom. Such tampon devices are disclosed in U.S. Pat. No. 4,412,833, entitled "Tampon Applicator", issued to Weigner, et al. on Nov. 1, 1983, and U.S. Pat. No. 4,413,986, entitled "Tampon Assembly With Means For Sterile Insertion", issued to Jacobs on Nov. 8, 1983.

Hybrid devices which attempt to merge the structural features of the sanitary napkins and the tampons into a single device have also been proposed. Such hybrid devices are disclosed in U.S. Pat. No. 2,092,346, entitled "Catamenial Pad", issued to Arone on Sep. 7, 1937, and U.S. Pat. No. 3,905,372, entitled "Feminine Hygiene Protective Shield", issued to Denkinger on Sep. 16, 1975. Other less intrusive hybrid devices are known as labial or interlabial sanitary napkins and are characterized by having a portion which at least partially resides within the wearer's vestibule and a portion which at least partially resides external of the wearer's vestibule. Such devices are disclosed in U.S. Pat. No. 2,662,527, entitled "Sanitary Pad", issued to Jacks on Dec. 15, 1953, and U.S. Pat. No. 4,631,062, entitled "Labial Sanitary Pad", issued to Lassen, et al. on Dec. 23, 1986.

Interlabial pads have the potential to provide even greater freedom from inconvenience because of their small size and reduced risk of leakage. Numerous attempts have been made in the past to produce an interlabial pad which would combine the best features of tampons and sanitary napkins while avoiding at least some of the disadvantages associated with each of these types of devices. Examples of such devices are described in U.S. Pat. No. 2,917,049 issued to Delaney on Dec. 15, 1959, U.S. Pat. No. 3,420,235 issued to Harmon on Jan. 7, 1969, U.S. Pat. No. 4,595,392 issued to Johnson, et al. on Jun. 17, 1986, and U.S. Pat. Nos. 5,074,855 and 5,336,208 issued to Rosenbluth, et al. on Dec. 24, 1991 and Aug. 9, 1994 respectively, and U.S. Pat. No. 5,484,429 issued to Vukos, et al. on Jan. 16, 1996. A commercially available interlabial device is FRESH 'N FIT® Padettes® which are marketed by Athena Medical Corp. of Portland, Oreg. and described in U.S. Pat. Nos. 3,983,873 and 4,175,561 issued to Hirschman on Oct. 5, 1976 and Nov. 27, 1979, respectively.

Generally, there are some drawbacks associated with the above products. For example, the device described in the Delaney patent does not appear to be capable of an easy and comfortable insertion, due to the possibility of the layers of absorbent material opening up during insertion. Thus, a need exists for an interlabial device that is small in size and that can be easily inserted and that provides protection against incontinence, menstrual discharges, and discharges of bodily exudates throughout a great range of wearer motions. A need also exists for an interlabial device that will reliably be expelled when the wearer urinates.

SUMMARY OF THE INVENTION

Accordingly, the present invention provides an absorbent device insertable into the interlabial space of a female wearer. The absorbent device comprises a main absorbent portion comprising an upper portion and a lower portion. The upper portion has a top surface facing toward the vestibule floor of the wearer during insertion into the interlabial space. The upper portion leads the lower portion during insertion of the absorbent device; i.e., the lower portion is spatially opposed to the upper portion, and upon insertion of the absorbent device into a wearer's interlabial space, the lower portion faces away from the vestibule floor of the wearer. Additionally, structures acting as an acquisition/transfer complex are positioned about and extend from the upper portion of the main absorbent portion. The fluid acquisition/transfer complex is configured to be in intimate contact with the folds and creases of the interlabial space of the female wearer. Furthermore, the fluid acquisition/transfer complex receives fluid from the folds and creases of a wearer's interlabial space and transfers fluid to the main absorbent portion.

Preferably, the fluid acquisition/transfer complex comprises hydrophilic fibers. The hydrophilic fibers may comprise a height from the top of the upper portion of the main absorbent portion to a wearer's folds and creases ranging from about 0.5 mm to about 5 mm. The hydrophilic fibers may comprise at least one type of fiber consisting of polyethylene, polypropylene, polyester, rayon, synthetic bi-component fibers and combinations thereof. Preferably, the hydrophilic fibers herein may comprise capillary channel fibers. Also additionally, any of the above-mentioned fibers may be crimped, twisted and/or curled, excluding any kinking of the capillary channel fibers.

In one embodiment herein, the fluid acquisition/transfer complex is attached at points along the top surface of the upper portion. In another embodiment herein, the fluid acquisition/transfer complex extends through the main absorbent portion and may further extend through the main absorbent portion and out thereof to another point above the upper portion top surface.

In practice, the absorbent device at least partially covers the wearer's urethra and orifice of the vagina upon proper positioning of the absorbent device. Also, the main absorbent portion of the device comprises a length from about 35 mm to about 120 mm and preferably from about 40 mm to about 100 mm. The caliper of the main absorbent portion may range from about 2 mm to about 12 mm, more preferably from about 3 mm to about 6 mm and also preferably be about 4.5 mm.

In another preferred embodiment herein, the absorbent device further comprises a liquid pervious topsheet positioned onto at least a portion of the main absorbent portion. Also, a backsheet may be positioned onto the device, and preferably onto the lower portion of the main absorbent portion.

In an alternative embodiment herein, the absorbent device further comprises a pair of extensions joined to the upper portion of the main absorbent portion. The extensions extend downwardly and outwardly from the main absorbent portion and are capable of maintaining contact with the inside surface's of the wearer's labia when the absorbent device is worn. Preferably, the extensions are capable of covering the fingertips of a wearer as the absorbent device is inserted into the interlabial space of the wearer. In like manner to insertion of the device, a wearer's fingers are also protected by the extensions when she removes the device from her interlabial space. The fluid acquisition/transfer complex, preferably substantially comprising fibers, may be positioned on the extensions to further facilitate the acquisition/transfer of fluid from a wearer to the absorbent device.

BRIEF DESCRIPTION OF THE DRAWINGS

While the specification concludes with claims particularly pointing out and distinctly claiming the subject matter which is regarded as forming the present invention, it is believed that the invention will be better understood from the following description taken in conjunction with the accompanying drawings, in which:

FIG. 4 is a perspective view of an alternative embodiment of the absorbent interlabial device of the present invention;

FIG. 5 is an end view of the absorbent device shown in FIG. 4;

FIG. 6 is an end view of an alternative embodiment of the absorbent interlabial device of the present invention;

FIG. 7 is a cross-sectional view of an alternative embodiment of the absorbent interlabial device of the present invention; and FIG. 8 is a cross-sectional view of an alternative embodiment of the absorbent interlabial device of the present invention.

DETAILED DESCRIPTION OF THE INVENTION

Figure 1:
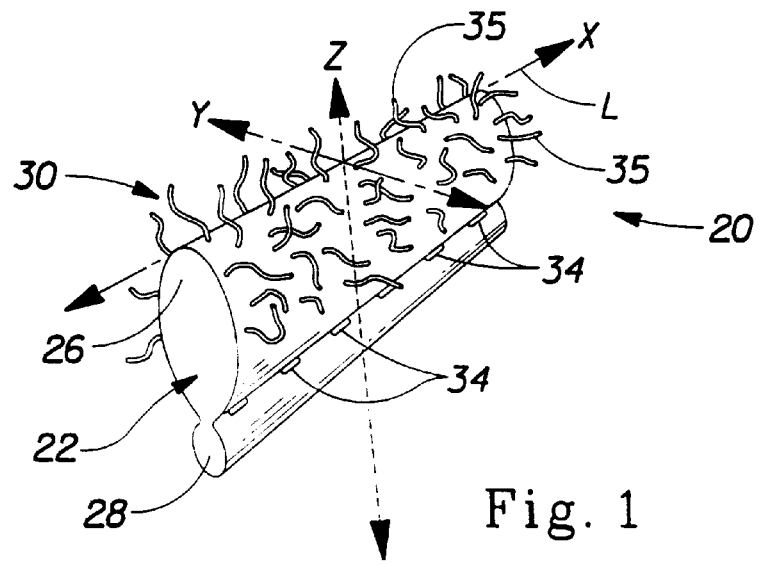
FIG. 1 is a perspective view of a preferred embodiment of the absorbent interlabial device of the present invention.

The present invention is directed to an absorbent interlabial device. FIG. 1 shows one preferred embodiment of the absorbent interlabial device of the present invention, interlabial device 20. The present invention, however, can be in many other forms, and is not limited to a structure having the particular configuration shown in the drawings.

As used herein the term "absorbent interlabial device" refers to a structure which has at least some absorbent components, and is specifically configured to reside at least partially within the interlabial space of a female wearer during use.

Preferably, more than half of the entire absorbent interlabial device 20 of the present invention resides within such interlabial space, more preferably substantially the entire absorbent interlabial device 20 resides within such interlabial space, and most preferably the entire absorbent interlabial device 20 resides within such interlabial space of a female wearer during use.

As used herein, the term "interlabial space" refers to that space in the pudendal region of the female anatomy which is located between the inside surfaces of the labia majora extending into the vestibule. Located within this interlabial space are the labia minora, the vestibule and the principal urogenital members including the clitoris, the orifice of the urethra, and the orifice of the vagina. Standard medical authorities teach that the vestibule refers to the space bounded laterally by the inside surfaces of the labia minora and extending interiorly to the floor between the clitoris and the orifice of the vagina. Therefore, it will be recognized that the interlabial space as defined above may refer to the space between the inside surfaces of the labia majora, including the space between the inside surfaces of the labia minora also known as the vestibule. The interlabial space for purposes of the present description does not extend substantially beyond the orifice of the vagina into the vaginal interior.

The term "labia" as used herein refers generally to both the labia majora and labia minora. The labia terminate anteriorly and posteriorly at the anterior commissure and the posterior commissure, respectively. It will be recognized by those skilled in the art that there is a wide range of variation among women with respect to the relative size and shape of labia majora and minora. For purposes of the present description, however, such differences need not be specifically addressed. It will be recognized that the disposition of the absorbent interlabial device into the interlabial space of a wearer as defined above will require placement between the inside surfaces of the labia majora without regard to the precise location of the boundary between the labia majora and the labia minora for a particular wearer. For a more detailed description of this portion of the female anatomy, attention is directed to *Gray's Anatomy*, Running Press 1901 Ed. (1974), at pp. 1025–1027.

The absorbent interlabial device 20 shown in FIG. 1 has a longitudinal centerline L which runs along the "x" axis shown in FIG. 1. The term "longitudinal", as used herein, refers to a line, axis or direction in the plane of the interlabial device 20 that is generally aligned with (e.g., approximately parallel to) a vertical plane which bisects a standing wearer into left and right body halves when the interlabial device 20 is worn. The terms "transverse," "lateral," or "y direction" as used herein, are interchangeable, and refer to a line, axis or direction that is generally perpendicular to the longitudinal direction. The lateral direction is shown in FIG. 1 as the "y" direction. The "z" direction, shown in FIG. 1, is a direction parallel to the vertical plane described above. The term "upper" refers to an orientation in the z-direction toward the wearer's head. "Lower" or downwardly is toward the wearer's feet.

As shown in FIG. 1, the interlabial device 20 comprises a main absorbent portion (or "central absorbent") 22. The main absorbent portion 22 should be at least partially absorbent. The main absorbent portion 22 may comprise non-absorbent portions, such as a liquid impervious barrier to prevent absorbed exudates from leaking out of the main absorbent portion 22. The main absorbent portion 22 comprises an upper portion 26 and a lower portion 28 that is opposed to the upper portion. In use, the upper portion 26 is positioned furthest inward into the wearer's interlabial space.

The interlabial device 20 should be of a suitable size and shape that allows at least a portion thereof to fit comfortably within the wearer's interlabial space and to cover the wearer's vaginal orifice, and preferably also the wearer's urethra. The interlabial device 20 at least partially blocks, and more preferably completely blocks and intercepts the flow of menses, urine, and other bodily exudates from the wearer's vaginal orifice and urethra.

Figure 2:
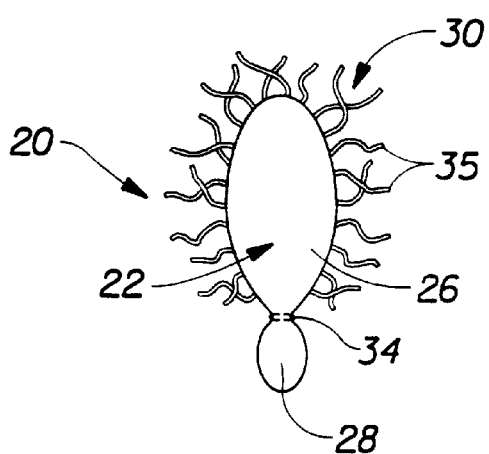
FIG. 2 is an end view of the absorbent device shown in FIG. 1.

FIGS. 1 and 2 also shows a network of fibers in the fluid acquisition/transfer complex 30 that preferably comprises fibrous elements or fibers 35. By the term "complex" it is meant herein a network of interrelated fibers of one or more types. Such fibers may be also, but not necessarily, interconnected. When the interlabial device 20 is inserted into the interlabial space of a female wearer, the fibers 35 conform to and contact the folds and creases of the female's interlabial space. At such contact, the fibers 35 are positioned to receive fluid (e.g., menses) from the body and to transfer such fluid to the main absorbent portion 22. Preferably the fluid acquisition/transfer complex 30 is hydrophilic so as to facilitate the ready transfer of fluid from the female to the main absorbent portion 22. Suitable materials for use in the fluid acquisition/transfer complex 30 are rayon (e.g., trilobed or multi-lobed rayon fibers), polyethylene, polypropylene, polyester, synthetic bi-component fibers, absorbent foams and combinations thereof, all of which fibers either singly or in combination with other fibers are known in the art. Furthermore, a highly preferred fiber 35 for use with the interlabial device 20 are capillary channel fibers. While not wishing to be bound to any particular theory, it is believed that the unique configurations and grooves formed within capillary channel fibers and tri-lobed or multi-lobed rayon fibers offers an enhanced transfer of fluid from a female wearer to the remainder of the device 20, e.g., the main absorbent portion 22.

In practice, the fluid acquisition/transfer complex 30 may be attached to the top surface of the main absorbent portion 22 (upper portion 26 and/or lower portion 28). Additionally, the fluid acquisition/transfer complex 30 may extend from some point within the main absorbent portion 22 or may even extend through the main absorbent portion 22 such that fibers 35 in the fluid acquisition/transfer complex 30 may have two exposed ends that contact a female's interlabial folds and crevices while extending through some segment of the main absorbent portion 22. Additionally, the fibers 35 of the fluid acquisition/transfer complex 30 may form loops 35' (FIG. 7). These loops 35' may be segmented as shown in FIG. 7 or more than one loop 35" may be made from one continuous or semi-continuous fiber 35" as shown in FIG. 8.

Most preferably, the fibers 35 will be oriented towards the surfaces of the labia vestibule of a female wearer from the surface of the upper portion 26 of the main absorbent portion 22. More specifically, the fibers 35 will be oriented towards the surfaces of the labia vestibule at a range of between 45° to 135° from the surface of the upper portion 26. More preferably, the fibers 35 will be oriented at about 90° from the surface of the upper portion 26. Such orientation of the fibers 35 is necessary to ensure that the fibers 35 will make substantial contact with the creases and folds of the labia vestibule of the female wearer. It is important that when the absorbent device 20 herein is inserted and worn, the fibers 35 thereon make substantial contact with the folds and creases of the labia vestibule of a wearer, and are not pressed-down away from the folds and creases of the labia vestibule.

The size of the interlabial device 20 is also important to the comfort associated with wearing the device. In the preferred embodiment shown in FIG. 1, the main absorbent portion 22 of the interlabial device 20 has a length as measured along the longitudinal centerline, L, of between about 35 mm and about 120 mm. Preferably, the length of the interlabial device 20 is between about 40 mm and about 100. The caliper (or width) of the main absorbent portion 22 of the interlabial device as measured in the transverse direction (or "y"-direction) may range from 2 mm to about 12 mm, more preferably the caliper is between about 3 mm and about 6 mm, most preferably, the caliper is about 4.5 mm. Caliper measurements given herein were measured using an AMES gauge with a 0.25 psi (gauge) load and a 20 mm diameter foot. Those skilled in the art will recognize that if a 20 mm diameter foot is not appropriate for a particular sample size, the foot size may be varied while the load on the gauge is accordingly varied to maintain a confining pressure of 0.25 psi (gauge). The height (or "z"-direction dimension) of the main absorbent portion 22 is preferably between about 8 mm and about 35 mm, and more preferably is about 20 mm.

The interlabial device 20 is preferably provided with sufficient absorbency to absorb and retain the exudates discharged from the wearer's body. The absorbent capacity of the product, however, is dependent at least partially upon the physical volume of the absorbent interlabial device 20, particularly the main absorbent portion 22 thereof. The main absorbent portion 22 preferably has an absorbent capacity of at least about 1 g of 0.9% by weight saline solution, and may have an absorbent capacity of up to about 30 g by using absorbent gels or foams that expand when wet. Absorbent Capacities may typically range from about 2 to about 10 grams, for saline. A method for measuring absorbent capacity is described in U.S. patent application Ser. No. 08/778,520 entitled "Absorbent Interlabial Device With Flexible Extensions", such patent application being incorporated herein by reference. Since the interlabial space can expand, larger volumes can be stored in the interlabial space, if the fluid is stored as a gel, which adjusts to the body pressures. Additionally, if the absorbent interlabial device 20 does not reside completely within the wearer's interlabial space, some of the absorbed exudates may be stored externally to the wearer's interlabial space.

Figure 3:
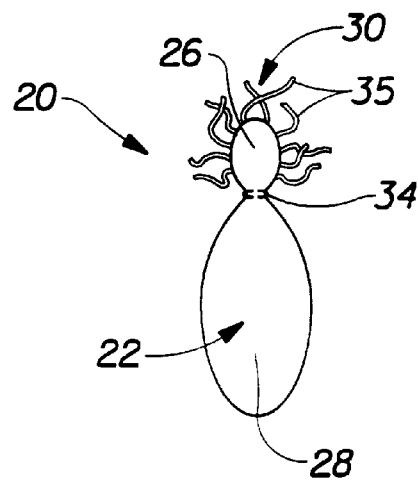
FIG. 3 is an end view of a variation of the preferred embodiment shown in FIG. 2.

The main absorbent portion 22 of the preferred embodiment shown in FIGS. 1–3 may comprise any suitable type of absorbent structure that is capable of absorbing and/or retaining liquids (e.g. menses and/or urine). The main absorbent portion 22 may be manufactured in a wide variety of shapes. Non-limiting examples include ovoid, trapezoidal, rectangular, triangular, cylindrical, hemispherical or any combination of the above. The main absorbent portion 22 may, likewise, be manufactured from a wide variety of liquid-absorbent materials commonly used in absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these. Preferred absorbent materials comprise folded tissues, woven materials, nonwoven webs, needle punched rayon, and thin layers of foam. The main absorbent portion 22 may comprise a single material or a combination of materials, such as a wrapping layer surrounding a central wadding comprised of a different absorbent material.

In the preferred embodiment shown in FIG. 1, the main absorbent portion 22 is formed of a soft absorbent material such as rayon fibers or other suitable natural or synthetic fibers or sheeting. The main absorbent portion 22 shown in FIG. 1 is generally of an ovoid cross sectional shape as shown in FIG. 2. The main absorbent portion 22 of the embodiment shown in FIGS. 1 and 2 comprises an upper portion 26 with a larger transverse sectional dimension relative to that of the lower portion 28. The upper portion 26 is preferably integral with the lower portion 28. In less preferred embodiments, however, the upper portion 26 and lower portion 28 may comprise separate elements joined together by any suitable means known in the art. In the preferred embodiment shown in FIGS. 1 and 2, the juncture of the upper portion 26 and lower portion 28 of the main absorbent portion 22 comprises a substantially abrupt change in the transverse dimension thereby forming a shoulder-like configuration at such juncture. In the preferred embodiment shown in FIGS. 1 and 2, the juncture of the upper portion 26 and lower portion 28 of the main absorbent portion 22 is formed by stitching 34.

In a variation of the preferred embodiment described above and shown in FIGS. 1 and 2, the upper portion 26 may have a smaller transverse sectional dimension relative to the transverse sectional dimension of the lower portion 28. An absorbent interlabial device 20 having such a configuration is shown in FIG. 3.

The main absorbent portion 22 can be made by any suitable process. U.S. Pat. No. 4,995,150 issued to Gerstenberger et al. on Feb. 26, 1991 and U.S. Pat. No. 4,095,542 issued to Hirshman on Jun. 20, 1978 describe methods for making absorbent devices which are suitable for use as the main absorbent portion 22 of the absorbent interlabial device 20 shown in FIGS. 1–3, each of which patents being hereby incorporated by reference herein.

As shown in FIG. 4, the absorbent interlabial device 120 may also comprise a pair of extensions 124 which are joined to the upper portion 126 of the main absorbent portion 122 of the absorbent interlabial device 120. In the embodiment shown in FIG. 4, the extensions 124 are generally rectangular in shape. Other shapes are also possible for the extensions 124 such as semi-circular, trapezoidal, or triangular. The extensions 124 preferably are from about 35 mm to about 160 mm in length, more preferably from about 45 mm to about 130 mm in length, and most preferably from about 50 mm to about 115 mm in length. While the extensions 124 can have a length (measured in the x-direction) which is shorter than the main absorbent portion 122, preferably they have a length which is the same as or longer than the main absorbent portion 122 of the absorbent interlabial device 120. The width of each extension refers to the distance from the attachment of flexible extension 124 to the main absorbent portion 122 (or the proximal end 124A of the flexible extension 124) to the distal end (or free end) 124B of the flexible extension 124 (FIG. 5). The width of the extensions 124 is preferably about equal to or greater than the height of the main absorbent portion as described above. The caliper of the extensions is preferably less than or equal to about 3 mm, more preferably less than or equal to about 2 mm, and most preferably less than or equal to about 1 mm. Ideally the caliper of the extensions 124 and the main absorbent portion 122 are selected such that the caliper of the overall absorbent interlabial structure 120 is less than or equal to about 8 mm. A more detailed discussion of this type of interlabial device, i.e., one having extensions, is disclosed in U.S. patent application Ser. No. 08/778,520, entitled "Absorbent Interlabial Device With Flexible Extensions", such discussion being incorporated herein by reference.

The term "joined", as used herein, encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element; i.e., one element is essentially part of the other element.

The stiffness of the main absorbent portion 22 is important for product comfort. If the main absorbent portion 22 is too flexible, the device is not conveniently or easily placed between the folds of the labia, if it is too stiff, the device is uncomfortable and when the user is in a sitting position, the product can be forced forward against the clitoris causing discomfort. The main absorbent portion 22 preferably has a stiffness approximately equal to that of the products described in U.S. Pat. Nos. 4,995,150 and 4,095,542. Such stiffness of the main absorbent portion 22 can be measured by the Three Point Bend Test as described in U.S. patent application Ser. No. 08/778,520 entitled "Absorbent Interlabial Device With Flexible Extensions", such patent application being hereby incorporated by reference herein.

FIG. 6 shows the interlabial device 20 comprising other optional components. For example, the interlabial device 20 may comprise a topsheet 42 positioned over and joined to all or a portion of the body facing surface of the device 20 and/or a backsheet 38 positioned over and joined to all or a portion of its back surface. When a topsheet 42 is applied to the interlabial device 20, the fibers 35, as shown in FIG. 6, are positioned such that they penetrate through the topsheet 42 and are connected to, preferably, the main absorbent portion 22 of the interlabial device 20. Preferably, if a topsheet 42 and/or a backsheet 38 is used, these components are joined to at least a portion of the main absorbent portion. In an alternative embodiment, the main absorbent portion could be at least partially wrapped by a topsheet 42.

If a topsheet is used, the topsheet should be compliant, soft feeling, and non-irritating to the wearer's skin. Further, the topsheet should be liquid pervious permitting liquids (e.g., menses and/or urine) to readily penetrate through its thickness. A suitable topsheet (and also extensions 124) may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, rayon, polypropylene, or polyethylene fibers) or from a combination of natural and synthetic fibers.

The topsheet may comprise an apertured formed film. Apertured formed films are pervious to body exudates and, if properly apertured, have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr, et al. on Jul. 31, 1984; and U.S. Pat. No. 5,006,394 "Multilayer Polymeric Film" issued to Baird on Apr. 9, 1991. The preferred topsheet for the present invention is the formed film described in one or more of the above patents and marketed on sanitary napkins by The Procter & Gamble Company of Cincinnati, Ohio as the "DRI-WEAVE" topsheet.

In a preferred embodiment of the present invention, the body surface of the formed film topsheet is hydrophilic (and likewise extensions 124) so as to help liquid to transfer through the topsheet faster than if the body surface was not hydrophilic so as to diminish the likelihood that menstrual fluid will flow off the topsheet rather than flowing into and being absorbed by the main absorbent portion 22. In a preferred embodiment, surfactant is incorporated into the polymeric materials of the formed film topsheet. Alternatively, the body surface of the topsheet can be made hydrophilic by treating it with a surfactant such as is described in U.S. Pat. No. 4,950,254 issued to Osborn, III.

If a backsheet is used, the backsheet could be impervious or semi-pervious to liquids (e.g., menses and/or urine) and is preferably flexible. As used herein, the term "flexible" refers to materials which are compliant and will readily conform to the general shape and contours of the human body. The backsheet prevents the exudates absorbed and contained in the main absorbent portion 22 from wetting articles which contact the absorbent interlabial device 20 such as the wearer's undergarments. The backsheet also assists the main absorbent portion 22 in preventing the wearer's body from being soiled by exudates. Additionally, use of the backsheet may provide an improved surface for the wearer to grasp between the fingers as the absorbent interlabial device 20 is inserted, or as the device is optionally removed with the fingers.

The backsheet may comprise a woven or nonwoven material, polymeric films such as thermoplastic films of polyethylene or polypropylene, or composite materials such as a film-coated nonwoven material. In one preferred option, the backsheet is a polyethylene film having a thickness of from about 0.012 mm (0.5 mil) to about 0.051 mm (2.0 mils). An exemplary polyethylene film is manufactured by the Clopay Corporation of Cincinnati, Ohio, under the designation P18-0401. A backsheet herein may permit vapors to escape from the main absorbent portion 22 (i.e., breathable) while still preventing exudates from passing through the backsheet.

As previously discussed, the absorbent interlabial device 20 of the present invention is preferably designed to be placed entirely within the interlabial space of a wearer. To use the absorbent interlabial device 20 of the present invention, the wearer holds the device at the upper portion 26 and/or lower portion 28 of main absorbent portion 22 between her fingers. In one embodiment shown in FIG. 4, the extensions 124 are spread apart so as to cover the tips of the wearer's fingers during insertion. This feature provides for a hygienic insertion of the absorbent interlabial device 120 of the present invention. The upper portion 126 is inserted first and furthest into the interlabial space. The wearer may assume a squatting position during insertion to assist in spreading the labial surfaces. Once the absorbent interlabial device 120 is inserted, the extensions 124 tend to adhere to the inside surfaces of the labia. When the wearer is standing, the labial walls close more tightly around the absorbent interlabial device 120 thereby folding the extensions 124 down around the interlabial device 120 and being at least in partial contact with the outer surface of the main absorbent portion 122.

The interlabial device 20 is preferably at least partially retained in place by exerting a slight laterally outwardly-oriented pressure on the inner surfaces of the wearer's labia minora, labia majora, or both. Additionally, the product is also held by attraction of naturally moist labial surfaces to the tissue comprising the extensions 24. Optionally, the fluid acquisition/transfer complex 30 may be provided with a bio-compatible adhesive to assist the adhesion of the interlabial device 20 to the inside surfaces of the wearer's labia. The strength of such an adhesive should be selected to assist the absorbent interlabial device 20 in staying in place, while still allowing for reliable, and comfortable removal of the device from the wearer's interlabial space.

The absorbent interlabial device 20 can be worn as a "stand alone" product. Alternatively, it can be worn as a back up to a tampon, or in combination with a sanitary napkin, pantiliner, or incontinence pad for menstrual or incontinence use. If the absorbent interlabial device 20 is used with a sanitary napkin, the sanitary napkin can be of any thickness. Use with a sanitary napkin may be preferred at night to reduce rear soiling. The interlabial device 20 can be worn in conventional panties, or it can be used with menstrual shorts.

Numerous alternative embodiments of the absorbent interlabial device of the present invention are possible. For example, these products are designed to be removed by urination, although an alternative extraction string or loop may be used. These products may also be used with medicinal treatments. These products may be constructed of materials which are biodegradable and/or which will fragment in water with agitation (as in a toilet). For example, U.S. patent application Ser. No. 08/883,606 entitled "Toilet-Disposable Absorbent Interlabial Device" describes a flushable interlabial device with water dispersible components, such patent application being incorporated herein by reference. Preferably, a toilet-disposable interlabial absorbent device 20 of the present invention will disperse into at least two fragments within two hours of exposure to mildly agitated room temperature water as described in the Water Dispersion Test in the TEST METHODS section, below. More preferably, the flushable interlabial absorbent device 20 will be dispersed into a plurality of fragments within about 60 minutes or, even more preferably within about 30 minutes and most preferably, within about 15 minutes as measured by the Water Dispersion Test. Preferably, the product will break into fragments which are smaller than about 6 in$^2$, more preferably smaller than about 2 in$^2$, most preferably smaller than about 1.5 in$^2$. In particularly preferred embodiments of the present invention, each of the components of the flushable interlabial absorbent device 20 will disperse into a plurality of fragments when immersed in mildly agitated water. Alternatively, the components of the absorbent interlabial device 20 may separate from each other without themselves breaking into a plurality of fragments (e.g. the flexible extensions 24 may break apart from the central absorbent portion 22 while each otherwise remains intact).

The term "toilet-disposable" as used herein includes the following characteristics of an absorbent interlabial device: flushability, dispersibility, and biodegradability. As used herein the terms "flushable" and "flushability" refer to a product's ability to pass though typically commercially available household toilets and plumbing drainage systems without causing clogging or similar problems that can be directly associated with the physical structure of the product. It is recognized, however, that there can be many differences between the various types of toilets available. Therefore, for the purposes of the appended claims, a test to determine the flushability of a catamenial product, such as an absorbent interlabial device, is set out in the TEST METHODS section of this specification.

The term "dispersible" as applied herein to an absorbent interlabial device refers to an article which will disperse into at least two fragments in mildly agitated water. Such a device will break into pieces in a conventional toilet and/or domestic plumbing system, and will ultimately be effectively processed though a sewage treatment system.

The term "biodegradable" as used herein refers to an absorbent device which is preferably at least partially constructed of biodegradable materials.

The absorbent interlabial device 20 may also be constructed with a plurality of slits in the main absorbent portion 22 so as to permit bending of the product in multiple independent directions. Such a structure allows the product to more easily respond to the stresses associated with body movements. In a preferred version of the embodiment shown in FIG. 4, the ends of the surface of the central absorbent facing away from the body may be rounded to reduce the force on the product during sitting. The top surface of the structure may have one or more slits or have other regions of preferred bending so that product may easily adjust to the vertical pressure against the pelvic floor, to help accommodate the non-linear surface of the pelvic floor between the clitoris and the perineum.

Tests for measuring absorbent capacity, flexibility, and burst strength of the interlabial device herein are disclosed in U.S. patent application Ser. No. 08/778,520, entitled "Absorbent Interlabial Device With Flexible Extensions", such patent application being incorporated herein by reference.

Capillary Channel Fiber Structure and Surface Properties

Preferred fibers for use herein and specifically for use in the fibrous elements 35 are capillary channel fibers. Suitable capillary channel fibers for use herein are described in European Patent Publication No. 391,814, published Oct. 10, 1990—this published application was filed in the name of the Eastman Kodak Company; U.S. Continuation-In-Part Application entitled "Fibers Capable of Spontaneously transporting Fluids", Ser. No. 07/736,267, published as PCT WO 93/02235 on Feb. 4, 1993 filed in the name of Phillips, et al. on Jul. 23, 1991, U.S. Pat. No. 5,200,248 entitled "Open Capillary Channel Structures, Improved Process for Making Capillary Channel Structures, and Extrusion Die for Use Therein" issued in the name of Thompson, et al. on Apr. 6, 1993; and, U.S. patent application Ser. No. 07/918,174 entitled "Spinerette Orifices and Filament Cross-Sections With Stabilizing Legs Therefrom", filed in the name of Phillips, et al. on Jul. 23, 1992. Suitable capillary channel fibers are also described in the following patent applications which were filed on Jul. 23, 1991: U.S. patent application Ser. No. 07/734,404 filed in the name of Thompson, et al.; U.S. patent application Ser. No. 07/734,392 filed in the name of Thompson, et al.; and, U.S. patent application Ser. No. 07/734,405 filed in the name of Buenger, et al. These patent applications may be referred to collectively as the "Capillary Channel Fiber" patent applications. The disclosure of all of the above patent applications and patent publications are incorporated herein by reference.

The fibers used herein can be prepared from any convenient polymer which is nonswelling when wet. Polymers such as polyethylene, polypropylene, polyesters (preferred), and the like, are useful herein, so long as they are spinnable such that they can be formed with external capillary channels, as noted herein above. Rayon and/or dacron fibers are also suitable for use as capillary channel fibers herein. Conveniently, the polymers are melt-extrudable. Typically, the capillary channel fibers herein will be prepared from a synthetic polyethylene terephthalate polymer melt having an inherent viscosity ("IV") of from about 0.6 to about 0.9.(IV is a term of art and can be determined in well-known fashion. See, for example, U.S. Pat. No. 4,829,761 at column 8.) The IV of a polymer melt bears some relationship to the ability of the polymer to retain the shape of the capillary channel walls, and is related to the average molecular weight of the polymers. For example, it is convenient to employ a polyester having an inherent viscosity of about 0.7 herein, but it would be more preferred to employ a polymer having an inherent viscosity of about 0.9, since this would allow the walls of the capillary channels to be thinner, yet sufficiently strong to avoid collapse under in-use pressure. Preferred capillary channel fibers herein have a denier (denier per filament "dpf") of about 10, and capillary channel fibers having such a fine denier, but whose walls are stable, can be achieved especially from polyester having an inherent viscosity of about 0.9. However, in commercial practice using such high IV polymers may require special processing equipment. As a quite acceptable compromise, and in order to achieve capillary to channel walls without in-use collapse, polyester/polymer having an inherent viscosity of about 0.7 can be employed at a denier per filament of about 22. However, it is to be understood that the denier of the fibers used is within the discretion of the formulator, and the denier per channel can easily be in the range of 25.

The depth:width ratio of the capillary channels herein is preferably about 2.0, but processing restrictions, as noted above, as well as for economic reasons, a depth:width ratio of about 1.3 is typically employed. Typical and readily producible capillary channel fibers which are quite satisfactory for use herein thus have a depth-of-walls of about 48 microns and a width-between-walls of about 37 microns. The walls, themselves, are typically about 3–15 microns thick. Although variations in these dimensions are acceptable, capillary channel fibers prepared from polyester and having these characteristics are quite effective for their intended purpose. Such fibers can be prepared using conventional operating equipment and readily withstand pressures of the type encountered in sanitary devices, especially sanitary napkins and pantiliners, without collapse or spreading of the capillary channel walls to such an extent that their capillary function is lost.

The capillary channels can be of various shapes. Certain shapes can offer particular advantages in particular product applications. For example, "U-shaped", "H-shaped", and "V-shaped" capillary channels may be used. The "H-shaped" fibers are one preferred shape. Furthermore, the basic shapes may be repeated (see Figures), or even branched, to produce fibers containing multiple channels, but it will be appreciated that when more than about three repeating shapes are used, some additional stiffness may be noted in the fibers. Other types of fiber designs configured to have multiple lobes (at least 3 or more) can be made from rayon. The use of rayon capillary fibers have the additional advantage of being biodegradable.

While the polymers used to prepare the capillary channel fibers herein are not, themselves, water-absorbent (nor are they absorbent to urine or blood-containing fluid such as menses), the fibers themselves are most preferably hydrophilic. Since most synthetic polymers are hydrophobic, the capillary channel fibers herein are surface-treated in order to render them hydrophilic. The surface treatment of polymeric fibers involves processes which are well-known in the extensive fiber literature, and such processes can be used herein. In general, such processes involve treating the surface of the fibers with a "hydrophilizing agent", especially a surfactant. (Hydrophilization, which results in wettability of the fibers by aqueous fluids, can routinely be measured, for example, using contact angle measurements. In general, a contact angle less than 90° indicates a hydrophilic surface. A CAHN Surface Force Analyzer (SFA 222) can be used to measure hydrophilicity, as can a variety of other instruments known in the art.) Typical surfactants useful in such processes include various nonionic and anionic detersive surfactants of the general type known in the laundry literature. Hydrophilizing agents include wetting agents such as polyethylene glycol monolaurates (e.g., PEGOSPERSE 200 ML, a polyethylene glycol 200 monolaurate available from Lonza, Inc., Williamsport, Pa., U.S.A.), and ethoxylated oleyl alcohols (e.g., VOLPO-3, available from Croda, Inc., New York, N.Y., U.S.A.). Other types of hydrophilizing agents and techniques can also be used, including those well known to those skilled in the fiber and textile arts for increasing wicking performance, improving soil release properties, etc. Hydrophilizing agents can be added to the polymer at various stages prior to use, though preferably prior to drawing of the capillary channel fibers to their final size. For example, the hydrophilizing agent can be added in advance to the polymer prior to melting or blended into the polymer subsequent to melting. The additive hydrophilizing agent can also be applied to the polymer subsequent to formation, e.g., subsequent to exit from an extrusion die in a melt, wet, or dry spinning process, preferably prior to drawing of the fiber to small diameter. Of course, since the articles herein are intended to come into contact with sensitive regions of the human body, it is preferred that surfactants used to hydrophilize the surfaces of the capillary channel fibers be nontoxic and nonirritating to human skin. Various surfactant treatments for hydrophilizing the capillary channel fibers are described in the Examples hereinafter. Another method for hydrophilizing fibrous surfaces involves subjecting said surfaces to ionizing radiation, e.g., in a plasma, and such methods have the advantage that there is no surfactant residue on the surface of the fibers. Whatever the means, the overall objective is to secure capillary channel fibers for use herein which are spontaneously wettable by the fluids they are intended to transport.

Capillary Channel Fiber Morphology

The capillary channel fibers herein have, as noted above and in the Figures, capillary channels on their outer surfaces. While the capillary channel fibers can also have a hollow central core which would provide some additional capillarity, it is preferred that such hollow core fibers not be employed. In general, providing capillary channel fibers with a central hollow core would require the fibers to be somewhat stiffer than desired in order that the core not collapse under pressure. A central core running through a capillary channel fiber would not be expected to quickly pick up fluids, since the fluids would have to find their way to the end of a fiber before proceeding into the core itself. Moreover, a hollow core capillary channel fiber could not release its load of fluid into an absorbent reservoir core without having appropriate contact between the ends of the hollow core fiber and the reservoir core material. To summarize: capillary channel fibers having external capillary channels offer substantial advantages in both pick-up and transfer of fluids, and the provision of a hollow core adds little in the way of performance advantages, but can impact negatively on the comfort level of an article made therewith in contact with the human body.

Moreover, the capillary channel fibers employed herein are preferably not in a straight-line configuration; rather, they are either bent or, most preferably, are in a curled configuration. It is easy to appreciate that capillary channel fibers that are nonlinear have, for a given number of fibers, a higher loft and increased resilience. By increasing the loft of the individual fibers, the overall loft of pads made therefrom is thicker and softer. This allows for the formation of low density, high loft pads which, assuming that the individual fibers themselves are not too thick or stiff (see denier, above), are extremely comfortable, yet effective for transporting fluids.

However, the preferred nonlinear capillary channel fibers herein should not be "kinked". As can also be readily appreciated, kinking a capillary channel fiber can cause points of constriction of the capillary channels at each kinking site. This, of course, would interfere with fluid flow dynamics along said capillary channel.

In addition to the foregoing, there is another substantial advantage to employing nonlinear capillary channel fibers. It is highly preferred that small portions, or "tufts", of the capillary channel fibers actually protrude into at least some of the topsheet orifices of the articles herein. As can be imagined, these protrusions are easier to effect when a high loft capillary channel pad is prepared using curled capillary channel fibers. Even by chance, there is a greater likelihood that a number of ends and/or curls in the capillary channel fibers will find their way into the orifices of the topsheet material than if substantially linear capillary channels were to be employed.

In a preferred mode, the capillary channel fibers herein are "substantially curled" (or otherwise gathered). As is known in the fiber art, fiber curling can be achieved by selectively heat quenching the fibers as they come from their forming die by heating one side of the fibers a bit more than the other side (or, conversely, by cooling one side more quickly than the other). Alternatively, fibers made from synthetic polymers such as polyesters can be curled by stretching, followed by relaxation, or by passing the fiber under tension around a sharp edge, followed by relaxation. Capillary channel fibers can also be curled by immersion in methanol. In a preferred mode, the fibers are substantially helical. Whatever means are used to crimp or otherwise curl the capillary channel fibers, they can, if desired, then be carded to form an assembly of fibers.

The preferred amplitude of the curls is in the range of about 0.1 mm to about 3 mm, and, typically, the frequency of the curls is from about 0.5 per cm of fiber to about 5 per cm of fiber. Fibers with amplitudes of about 3 mm and a frequency of about 0.5 per cm exhibit good softness even in the higher denier ranged fibers having large capillary channels. Stated otherwise, an average capillary channel fiber having a straight-line length of about 2 cm is curled or gathered to provide optimal fibers having a length of from about 0.5 cm to about 1.5 cm.

TEST METHODS
Water Dispersion Test

Apparatus

| | |
|---|---|
| Stirrer | Magnetic, Thermolyne type Model S7225 or 7200 (no substitutions). Permanently inscribe a circle 3.5 inches (8.9 centimeter) on the top surface of the stirrer. The center of the circle must be coincident with the geometric center of the stirrer. |
| Stirring Bar | 2.5 inch (6.2 centimeter) TEFLON coated with spinning ring. Permanently mark one end of the bar with black ink for a distance of 0.5 inch (1.2 centimeter) back from the tip. |
| Thermometer | 30 to 120° F. with 1 degree divisions |
| Timer | Digital stopwatch |
| Stroboscope | Variable speed stroboscope, model 964 available from Strobette, Power Instrument, Inc. of Skokie, IL is suitable |
| Beaker | Kimax brand 2000 milliliter with spout (no substitution), Inscribe a fill mark at a height of 5.6 inches (14.3 centimeters) from the flat bottom of the beaker. Do not use any beaker not having a flat bottom. |

-continued

TEST METHODS
Water Dispersion Test

Apparatus

| Conditioned Room | Temperature and humidity should be controlled to remain within the following limits:<br>Temperature: 73 ± 3° F. (23° C. ± 2° C.)<br>Humidity: 50 ± 2% Relative Humidity |
|---|---|

Test Setup
1. Fill the beaker to the fill mark with 73±3° F. tap water.
2. Place the beaker on the magnetic stirrer centering it in the inscribed circle.
3. Add the stirring bar to the beaker.
4. Turn the stroboscope on and set the speed to 1000 rpm according to the manufacturer's directions.
5. Turn the magnetic stirrer on with the on/off switch. Adjust the speed of the magnetic stirrer until the stirring bar appears to be stationary and both ends appear to be black. This indicates that the magnetic stirrer is turning at 500 rpm (i.e. half the setting on the stroboscope). Turn the magnetic stirrer off with the on/off switch.

Procedure
1. Hold a sample (e.g. an absorbent interlabial device 20) 3 to 4 inches (7.6 to 10.2 centimeters) above the surface of the water. Gently drop the sample onto the water surface, starting the timer when the sample touches the water surface.
2. Wait 5 seconds.
3. Start the magnetic stirrer with the on/off switch. If the sample disrupts the rotation of the stirring bar, stop the stirrer, re-orient the bar, and immediately start the stirrer again.
4. Record the time required until the sample separates into at least two pieces. Separation does not include the dissasociation of a few individual fibers from an otherwise intact sample. The time is the total time the sample is immersed in the water including the time the stirrer may have been stopped to re-orient the sample.
5. Repeat steps 1 through 4 with an additional 3 samples.

Calculation and Reporting
Calculate and report the mean and standard deviation of the water dispersibility time for the four samples tested.

Flushability Test
Overview

As noted above, the terms "flushable or flushability" refer to a product's capacity to pass through typical commercially available household toilets and plumbing drainage systems without causing clogging or similar problems that can be directly associated with the physical characteristics of the product. For the purpose of the appended claims, catamenial products are evaluated for flushability via relative ease of toilet bowl and trap evacuation and subsequent transport through a simulated plumbing system. The flushability of such a device should be measured by the following test procedure.

The test procedure is designed to simulate two days of normal toilet usage for a family of 4 (2 men, 2 women). The test employs a flushing sequence to simulate the following conditions: male urination visits, female urination visits (including post urinary drying with tissue), disposal of catamenial product (that is, the interlabial device or other device to be tested) with cleaning using tissue, and bowel movement visits. The amount of tissue to be used for each tissue flush is a normal loading of 2 strips of seven sheets. The normal loading is based on consumer research regarding typical habits and practices. The test is designed to simulate the conditions a product will encounter if it is flushed through a conventional toilet and into a municipal sewer or into a septic tank. Samples are evaluated for: 1) toilet bowl and trap clearance, 2) drain line blockage, and 3) disintegration during flushing.

Apparatus

An apparatus suitable for the flushability test is shown in plan view in FIG. 12. The apparatus includes:

a 3.5 gallon (13.2 liter) water saver siphon vortex toilet referred to as 210 (additional toilets can also be attached to the piping layout shown in FIG. 12 to evaluate the behavior of test samples using different flushing mechanisms such as commercial, pressure toilets);

approximately 59 feet (18 meters) of 4 inch (10 cm) inside diameter acrylic pipe (As can be seen from FIG. 14, the piping is assembled in roughly a square configuration having linear runs 211, 213, 215, 217, 219, 221 approximately 10 feet (3 meters) long);

a cast iron tee 223 slightly downstream of the toilet 210 that is open to the atmosphere for venting;

five cast iron ninety degree elbows 212, 214, 216, 218, and 220;

a snag 222 positioned vertically (FIG. 13) approximately 15 feet from the pipe's terminal end and approximately 1 inch (2.5 cm) long; and a screen (No. 4 Tyler sieve) to capture solid effluent for evaluation of disintegration.

The apparatus used for this method is set up to be equivalent to ANSI Standard A112.19.2M-1990 for Vitreous China fixtures. The piping is plumbed to provide a drop of 0.25 inch per foot (2 centimeters/meter) of pipe length.

Materials

Tissue Product used in Test: standard CHARMIN® toilet tissue manufactured by The Procter & Gamble Company of Cincinnati, Ohio.

Synthetic Fecal Material Prepared according to the method described below

Test Flushing Sequence

The test flushing sequence simulates 2 days of normal toilet usage for a family of 4 (2 men, 2 women; based on consumer habits and practices research). The sequence of 34 total flushes consists of 14 flushes with an empty bowl, 8 flushes with tissue only, 6 flushes with tissue and a catamenial product and 6 flushes with tissue and simulated fecal matter (SFM). When it is used, the SFM is placed in the bowl just prior to the addition of tissue. The SFM loading of 160 g±5 g consists of two 1 inch (2.5 centimeter)×4 inch (10 centimeter) pieces and one 1 inch (2.5 centimeter)×2 inch (5 centimeter) piece. Folded tissue strips (or the catamenial product) are placed in the bowl at 10 second intervals. Ten seconds after the final strip or catamenial product is placed into the bowl, the toilet is flushed. The flushing sequence is described below as a series of two routines combined in the following order:

Routine #1 (To be performed first 6 times for a total of 30 flushes)
1) Flush With Tissue Only—Take a drain line blockage reading 2 minutes after the water reaches the simulated obstruction, wait 1 additional minute, and move to step 2.

2) Flush With Empty Bowl. Take a drain line blockage reading 2 minutes after the water reaches the snag point and move to step 3.
3) Flush With Tissue and Catamenial Product—Take a drain line blockage reading 2 minutes after the water reaches the snag point, wait 1 additional minute, and move to step 4.
4) Flush With Empty Bowl. Take a drain line blockage reading 2 minutes after the water reaches the snag point and move to step 5.
5) Flush With Tissue and Simulated Fecal Matter (SFM). Take a drain line blockage reading 2 minutes after the water reaches the snag point, wait 1 additional minute.

Routine #2 (To be performed 1 time)
1) Flush With Tissue Only—Take a drain line blockage reading 2 minutes after the water reaches the snag point, wait 1 additional minute, and move to step 2.
2) Flush With Empty Bowl. Take a drain line blockage reading 2 minutes after the water reaches the snag point and move to step 3.
3) Flush With Tissue Only—Take a drain line blockage reading 2 minutes after the water reaches the snag point, wait 1 additional minute, and move to step 4.
4) Flush With Empty Bowl. Take a drain line blockage reading 2 minutes after the water reaches the snag point.

Total number of flushes per sequence is 34.

If, after the second flush in the flushing sequence, the product remains in the bowl or trap after flushing, the tissue and or catamenial product is plunged into the drainage line manually and the flushing sequence will continue. After completion of each trial loading, the drainage pipe will be cleared prior to beginning subsequent testing.

The above described flushing sequence is repeated three times for each test product.

Data Reporting

The degree of drain line blockage is determined by measuring the length of water dammed up behind the obstruction. Graduations are marked every 12 inches (30 centimeters) on the drainpipe upstream of the obstruction. Each one foot length that the water is backed up corresponds to 0.25 inch (0.6 centimeter) or 6.25% of blockage at the obstruction point. Test product residues which exit the drainpipe are also collected.

The following data are recorded for each evaluation:
1) Incidence of failure (%) of catamenial product to clear bowl and trap in one flush
2) Incidence of failure (%) of catamenial product to clear bowl and trap in two flushes
3) Incidence of product on simulated snag
4) Maximum level (%) of drain line blockage
5) Cumulative level (%) of drain line blockage over the 2 day simulated test period.

Preferably, the products described herein will completely clear the bowl at least about 70% of the time in two or fewer flushes, more preferably at least about 80% of the time in one flush, even more preferably at least about 90% of the time in one flush, and most preferably at least about 95% of the time in one flush. The products described herein will preferably have a maximum level of drain line blockage of less than or equal to about 80%. The products described herein will preferably have a cumulative level of drain line blockage over the 2 day simulated test period of less than or equal to about 50%.

Preparation of Synthetic Fecal Material
I. Materials Needed:
Feclone synthetic fecal matter (900 grams); (Available from Siliclone Studio, Valley Forge, Pa. as product BFPS-7 dry concentrate )
Tap water at 100° C. (6066 grams)
II. Equipment Needed:
Mixer (Available from Hobart Corp., Troy, Ohio as Model A200)
Extruder (Available from Hobart Corp., Troy, Ohio as Model 4812)
Disposable Centrifuge tubes with screw caps (50 ml) (Available from VWR Scientific, Chicago, Ill. as Catalog No. 21-008-176)
Water Bath to control temperature to 37° C.
III. Preparation:
1. Pour the 100° C. water into the mixing bowl of the mixer and add the dry Feclone concentrate.
2. Mix on low for 1 minute.
3. Mix on medium speed for 2 minutes.
4. After the material is well mixed, transfer to the extruder.
5. Using an ice pick, punch a small hole in the tip of each centrifuge tube.
6. Extrude the Feclone into the centrifuge tubes.
7. Cap the centrifuge tubes and store in the refrigerator.
8. Before using, put the tubes in the water bath at 38° C. This concludes the test.

The disclosure of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

While particular embodiments of the present invention have been illustrated and described, it would be obvious to those skilled in the art that various other changes and modifications can be made without departing from the spirit and scope of the invention.

What is claimed is:

1. An interlabial absorbent device to be placed at least partially within the interlabial space of a female wearer, said absorbent device comprising:

a main absorbent portion for storing received fluids having an upper portion and a lower portion thereof, said upper portion having a top surface facing toward the vestibule floor of the wearer during insertion within the interlabial space and leading said lower portion during insertion therein, said lower portion being opposed to said upper portion and upon insertion of said absorbent device into the interlabial space, said lower portion facing away from the vestibule floor of the wearer;

a pair of planar ends having a length therebetween; and a fluid acquisition/transfer complex connected to, positioned about and extending outwardly from said upper portion of said main absorbent portion, said fluid acquisition/transfer complex configured to be in intimate contact with the folds and creases of the interlabial space of the female wearer so that said fluid acquisition/transfer complex acquires and transports fluid from the folds and creases of the interlabial space to said main absorbent portion, said fluid acquisition/ transfer complex further comprising hydrophilic fibers extending outwardly from said absorbent portion a distance ranging from between about 0.5 mm to about 5 mm.

2. The interlabial absorbent device of claim 1 wherein said main absorbent portion comprises a width ranging from about 2 mm to about 12 mm.

3. The interlabial absorbent device of claim 2 wherein said width of said main absorbent portion ranges from about 3 mm to about 6 mm.

4. The interlabial absorbent device of claim 3 wherein said width of said main absorbent portion is about 4.5 mm.

5. The interlabial absorbent device of claim 1 wherein said main absorbent portion comprises a length of from about 35 mm to about 120 mm.

6. The interlabial absorbent device of claim 5 wherein said main absorbent portion comprises a length of from about 40 mm to about 100 mm.

7. The interlabial absorbent device of claim 1 wherein at least a portion of said fibers are attached to said top surface of said upper portion.

8. The interlabial absorbent device of claim 7 wherein a plurality of said fibers extends through said main absorbent portion to another point outwardly from said upper portion.

9. The interlabial absorbent device of claim 1 wherein said hydrophilic fibers comprise fibers selected from the group consisting of capillary channel fibers, tri-lobal rayon fibers, multi-lobal rayon fibers, and combination thereof.

10. The interlabial absorbent device of claim 1 wherein said hydrophilic fibers comprise materials selected from the group consisting of rayon, polyethylene, polypropylene, polyester, synthetic bi-component fibers, and combinations thereof.

11. The interlabial absorbent device of claim 1 wherein said absorbent device at least partially covers the wearer's urethra and orifice of the vagina upon positioning of said device.

12. The interlabial absorbent device of claim 1 wherein said absorbent device further comprises a liquid pervious topsheet positioned over at least said upper portion of said main absorbent portion such that said fibers extend from said main absorbent portion and outwardly through said topsheet.

13. The interlabial absorbent device of claim 1 wherein said absorbent device further comprises a liquid impervious backsheet joined to at least said lower portion of said main absorbent portion.

14. An interlabial absorbent device insertable into the interlabial space of a female wearer said absorbent device comprising:

a main absorbent portion having an upper portion and a lower portion thereof, said upper portion having a top surface facing toward the vestibule floor of the wearer during insertion into the interlabial space and leading said lower portion during insertion therein, said lower portion being opposed to said upper portion and upon insertion of said absorbent device into the interlabial space said lower portion facing away from the vestibule floor of the wearer;

a pair of extensions joined to said upper portion of said main absorbent portion, said pair of extensions extending downwardly and outwardly therefrom and being capable of maintaining contact with the inside surfaces of the wearer's labia when said absorbent device is worn; and a fluid acquisition/transfer complex connected to, positioned about and extending outwardly from said pair of extensions, said fluid acquisition/transfer complex configured to be in intimate contact with the folds and creases of the interlabial space of the female wearer, said fluid acquisition/transfer complex acquiring and transporting fluid from the folds and creases of the interlabial space to said pair of extensions and down to said main absorbent portion when the absorbent device is in use, said fluid acquisition/transfer complex further comprising hydrophilic fibers extending outwardly from said absorbent portion a distance ranging from between about 0.5 mm to about 5 mm.

15. The interlabial absorbent device of claim 14 wherein said main absorbent portion comprises a caliper ranging from about 2 mm to about 12 mm.

16. The interlabial absorbent device of claim 15 wherein said caliper of said main absorbent portion ranges from about 3 mm to about 6 mm.

17. The interlabial absorbent device of claim 16 wherein said caliper of said main absorbent portion is about 4.5 mm.

18. The interlabial absorbent device of claim 14 wherein said main absorbent portion comprises a length from about 35 mm to about 120 mm.

19. The interlabial absorbent device of claim 18 wherein said main absorbent portion comprises a length from about 40 mm to about 100 mm.

20. The interlabial absorbent device of clam 14 wherein said pair of extensions are capable of covering the fingertips of the wearer as said absorbent device is inserted into the interlabial space of the wearer.

21. The interlabial absorbent device of claim 20 wherein said extensions are further capable of covering the fingertips of the wearer as said absorbent device is removed from the interlabial space of the wearer by grasping said lower portion of said main absorbent portion of said absorbent device.

22. The interlabial absorbent device of claim 14 wherein said hydrophilic fibers comprise capillary channel fibers, tri-lobal rayon fibers, multi-lobal rayon fibers and combinations thereof.

23. The interlabial absorbent device of claim 14 wherein said hydrophilic fibers comprise material selected from the group consisting of rayon, polyethylene, polypropylene, polyester, synthetic bi-component fibers and combinations thereof.

24. The interlabial absorbent device of claim 14 wherein at least a portion of said fluid acquisition/transfer complex is attached at points along said extensions.

25. The interlabial absorbent device of claim 24 wherein at least a portion of the fluid/acquisition complex extends through at least a portion of said extensions.

26. The interlabial absorbent device of claim 14 wherein said absorbent device at least partially covers the wearer's urethra and orifice of the vagina upon positioning of said device.

27. The interlabial absorbent device of claim 14 wherein said absorbent device further comprises a liquid pervious topsheet positioned over at least said upper portion of said main absorbent portion.

28. The interlabial absorbent device of claim 14 wherein said absorbent device further comprises a liquid impervious backsheet joined to at least said lower portion of said main absorbent portion.

29. The interlabial absorbent device of claim 14 having water dispersible and flushable components for the flushing of said absorbent device into a toilet.

* * * * *